(12) United States Patent
Tu et al.

(10) Patent No.: US 10,973,779 B2
(45) Date of Patent: Apr. 13, 2021

(54) ASTAXANTHIN COMPOUND COMPOSITION AND THE METHOD THEREOF

(71) Applicant: Bioptik Technology, Inc., Hsinchu (TW)

(72) Inventors: Yao-Jen Tu, Hsinchu (TW); Chin-Chang Yang, Hsinchu (TW); Yu-Shan Liu, Hsinchu (TW); Chun-Lan Lo, Hsinchu (TW); Hui-Lan Kuo, Hsinchu (TW); Yi-Lung Wu, Hsinchu (TW); Yi-Hong Yang, Hsinchu (TW)

(73) Assignee: Bioptik Technology, Inc., Hsinchu (TW)

( * ) Notice: Subject to any disclaimer, the term of this patent is extended or adjusted under 35 U.S.C. 154(b) by 15 days.

(21) Appl. No.: 16/689,990

(22) Filed: Nov. 20, 2019

(65) Prior Publication Data
US 2020/0289433 A1    Sep. 17, 2020

(30) Foreign Application Priority Data

Mar. 14, 2019 (TW) ................................ 108108587

(51) Int. Cl.
| A61K 36/00 | (2006.01) |
| A61K 31/122 | (2006.01) |
| A61K 36/05 | (2006.01) |
| A61K 31/198 | (2006.01) |
| A61K 36/815 | (2006.01) |
| A61K 36/725 | (2006.01) |

(52) U.S. Cl.
CPC .......... *A61K 31/122* (2013.01); *A61K 31/198* (2013.01); *A61K 36/05* (2013.01); *A61K 36/725* (2013.01); *A61K 36/815* (2013.01)

(58) Field of Classification Search
CPC ..................................................... A61K 36/00
USPC ........................................................ 424/725
See application file for complete search history.

(56) References Cited

FOREIGN PATENT DOCUMENTS

CN    106389784    *    2/2017

* cited by examiner

*Primary Examiner* — Michael V Meller
(74) *Attorney, Agent, or Firm* — Muncy, Geissler, Olds & Lowe, P.C.

(57) ABSTRACT

The invention relates to an astaxanthin compound composition, the preparation system and the method of preparing the astaxanthin compound composition. The astaxanthin compound composition comprises *Haematococcus pluvialis* ingredient, extract of wolfberry, extract of jujube, and arginine. The preparation system includes a mixing unit and an additive-adding unit, those which operate sequentially to prepare a compound astaxanthin compound composition, the invention thus provides a stable and sustainably active compound astaxanthin compound composition with long shelf-life, which can bring favorable effects on regulating the lipid profile.

4 Claims, 2 Drawing Sheets

ASTAXANTHIN COMPOUND COMPOSITION AND THE METHOD THEREOF

CROSS-REFERENCE TO RELATED APPLICATIONS

This application claims the benefit of TW Application No. 108108587, filed on Mar. 14, 2019 the content of which are hereby incorporated by reference in their entirety.

FIELD OF THE INVENTION

The invention relates to an astaxanthin compound composition. In particular, the invention relates to the an astaxanthin compound composition containing specific compound composition, as well as the preparation method and the preparation system for the astaxanthin compound composition, which are used for improving health.

BACKGROUND OF THE INVENTION

Astaxanthin is a natural antioxidant, which belongs to carotenoids. Astaxanthin has excellent antioxidative capacity, especially the ability of scavenging free radicals, which is far better than beta-carotene, lutein and vitamin E. Recent studies reveal that the antioxidative capacity of astaxanthin can also improve cardiovascular health. The advantageous effects are primarily accomplished by reducing the accumulation of oxidized low-density lipoproteins in blood, and thus exhibiting superior benefits for human health. Therefore, astaxanthin has considerable potential for application in food, cosmetics, dietary supplements and healthcare.

However, because astaxanthin is insoluble in water and has unstable structure, it is susceptible to environmental factors such as light, heat, temperature, oxygen, acids and bases, metal ions, and moisture; and thus, the activity and effects may be impaired. Astaxanthin itself is hard to sustainably stored, which results in limited application. Therefore, there is still a need for improving a preparation system and a method of preparing astaxanthin-containing products.

Generally, the sources of astaxanthin are crustacean aquatic animals (shrimp, crab or its waste), green microalgae and certain types of yeast, but the available concentration of astaxanthin content are too low to sufficiently supply dietary supplements and healthcare products. In addition, if astaxanthin is extracted from aquatic animals, food allergies may become the utmost concern for certain population, and the extraction quality and mass production efficiency of astaxanthin become a major limitation for applications.

Therefore, in this technical field, the primary goal is to elaborate the benefits of astaxanthin by optimize the source, formulation and quality of astaxanthin.

SUMMARY OF THE INVENTION

An objective of the present invention is to provide an astaxanthin compound composition that has excellent stability, which can regulate the blood lipid profile.

According to the abovementioned objective, the present invention discloses an astaxanthin compound composition, which includes an ingredient derived from *Haematococcus pluvialis* (*H. pluvialis*), an extract of jujube, an extract of wolfberry, and arginine; wherein the weight percentage concentration of the ingredient derived from *H. pluvialis* ranges from 10% to 90%; the weight percentage concentration of the jujube extract ranges from 0.1% to 5%; the weight percentage concentration of the wolfberry extract ranges from 0.1% to 5%; and the weight percentage concentration of arginine ranges from 9% to 90%.

According to the abovementioned objective, the present invention further discloses an astaxanthin compound composition which includes ingredient derived from *H. pluvialis*. The ingredient derived from *H. pluvialis* of the astaxanthin compound composition contains astaxanthin, and the weight percentage concentration of the astaxanthin within the ingredient derived from *H. pluvialis* ranges from 1% to 20%, can also be ranges from 5% to 10% or 10% to 20%, and the preferred weight percentage ranges from 1% to 5%.

According to the abovementioned object, the present invention further discloses an astaxanthin compound composition, which further includes polysaccharide. The polysaccharide is selected from the group consisting of hyaluronic acid, hyaluronan, sodium hyaluronate, gum arabic, modified starch, hydrolyzed starch, maltodextrin, alginate, carrageenan, chitin, chitosan, cellulose, and combinations thereof.

According to the abovementioned objective, the present invention discloses an astaxanthin compound composition, which further includes anticaking agent. The weight percentage concentration of the anticaking agent within the astaxanthin compound composition ranges from 0.5% to 3%. The anticaking agent is selected from the group consisting of calcium silicate, silicon dioxide, potassium ferrocyanide, tricalcium phosphate, magnesium oxide, microcrystalline cellulose, cyclodextrin, activated charcoal, kaolin and combinations thereof.

According to the abovementioned objective, the present invention discloses an astaxanthin compound composition preparation system, which includes a mixing unit and an additive-adding unit. The mixing unit is used to add an wolfberry extract, a jujube extract, and an amino acid to an astaxanthin clathrate to form a well-mixed compound mixture. Then, the additive-adding unit is used to add the anticaking agent to the compound mixture to form the astaxanthin compound composition.

According to the abovementioned objective, the present invention further discloses a preparation method for astaxanthin compound composition, which includes the following steps: (1) an astaxanthin clathrate is provided; (2) a mixing step is performed to form a compound mixture, in which the mixing step is used to add a wolfberry extract, a jujube extract, and an amino acid ingredient to the astaxanthin clathrate to form a well-mixed compound mixture; and (3) an adding step is performed to add the anticaking agent to the compound mixture to form the astaxanthin compound composition. In some preferred embodiments of the present invention, the amino acid ingredient is arginine.

DETAILED DESCRIPTION OF EMBODIMENTS

In the following detailed description, numerous specific details are set forth to provide a thorough understanding of technical features and advantages of the claimed subject matter. Preferred embodiments are further provided for those skilled in the art to practice the claimed subject matter.

The accompanying drawings are referenced for better understating and ease of description, and those drawings are not necessarily drawn to scale. The technical contents that are known to those skilled in the art not described in detail herein.

The present invention discloses an astaxanthin compound composition, which includes an ingredient derived from *H. pluvialis*, a wolfberry extract, a jujube extract, and arginine, wherein the ingredient derived from *H. pluvialis* is the main source of the astaxanthin. In order to improve the health benefits, according to a preferred embodiment according to the present invention, the weight percentage concentration of the ingredient derived from *H. pluvialis* ranges from 10% to 90%, and preferably ranges from 10% to 30%. In addition, the weight percentage concentration of the red rate extract ranges from 0.1% to 5%; the weight percentage concentration of the wolfberry extract ranges from 0.1% to 5%; and the weight percentage concentration of arginine ranges from 9% to 90%, and preferably ranges from 10% to 50%.

Figure 1:
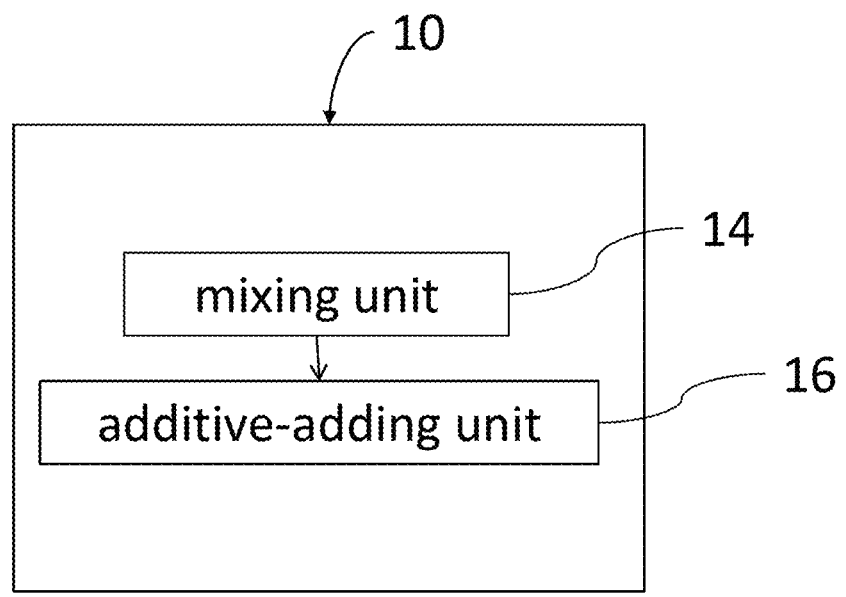
FIG. 1 is a block diagram of a preparation system for preparing an astaxanthin compound composition according to the present invention.

Next, please refer to FIG. 1, which is a block diagram of a preparation system of an astaxanthin compound composition according to the present invention. The astaxanthin compound composition preparation system 10 includes two units: a mixing unit 14 and an additive-adding unit 16, which are sequentially used to prepare astaxanthin compound composition. According to a preferred embodiment of the present invention, the astaxanthin compound composition preparation system 10 start with providing astaxanthin clathrate, which is stable and is capable of stably maintaining the activity of astaxanthin to be used in the astaxanthin compound composition preparation system 10. In the astaxanthin compound composition preparation system 10, the main function of the mixing unit 14 is to add other active ingredients to the astaxanthin clathrate to prepare a well-mixed compound mixture, wherein the active ingredients preferably include wolfberry extract, jujube extracts and amino acid such as arginine. The main function of the additive-adding unit 16 is to add safe and qualified food additives to compound mixture, with the purpose of adsorbing the oily content and moisture in the product, and thus it finally forms a stable, sustainably active astaxanthin compound composition with long-shelf life.

Figure 2:
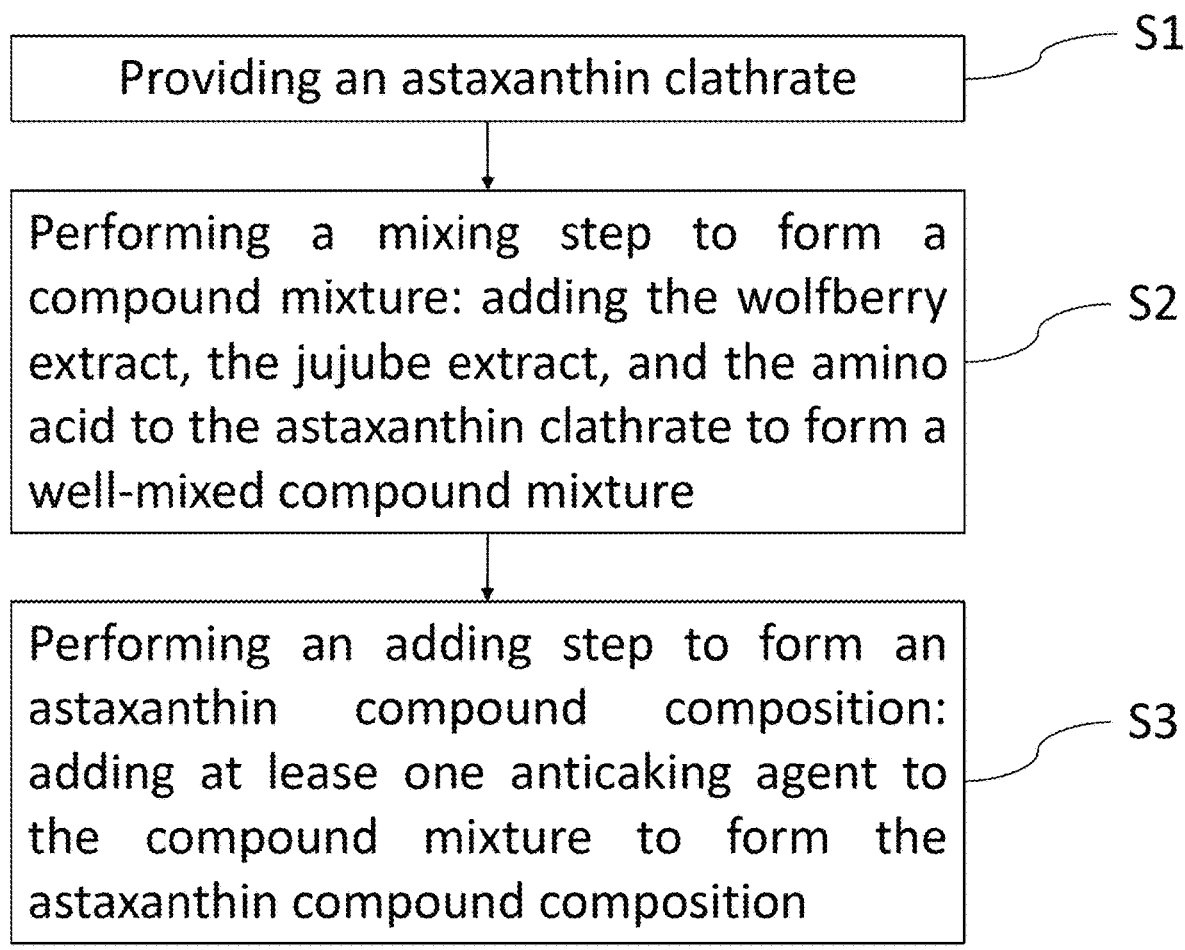
FIG. 2 is a flow chart showing the steps for preparing an astaxanthin compound composition according to the present invention.

Please also refer to FIG. 2, which is a flow chart showing the steps for preparing an astaxanthin compound composition according to the present invention. Step S1: the astaxanthin clathrate is provided to be used in the subsequent steps. The source or type of astaxanthin clathrate is not to be limited herein. As long as the astaxanthin within astaxanthin clathrate is capable of highly stable, sufficient and sustainable active, the astaxanthin clathrate can be applied in the present invention. Step S2: a mixing step is performed to form a compound mixture. Specifically, in the mixing step, the wolfberry extract, the jujube extract, and the amino acid are added to the astaxanthin clathrate to form a well-mixed compound mixture. Next, Step S3: an adding step is performed to form an astaxanthin compound composition. Specifically, in the adding step, the anticaking agent is added to the compound mixture to form the astaxanthin compound composition. More details about the implementation of the aforementioned steps are detailed in the following description.

Regarding the source of astaxanthin, the main source of astaxanthin on the market is crustacean aquatic animals (includes the waste of crustacean aquatic animals) such as shrimp, crab, microalgae and yeast (such as *Phaffia rhodozyma*), etc. Based on the concerns of food allergies and vegetarian consumer demand, the present invention preferably utilizes the ingredient derived from *H. pluvialis* as the source material. The ingredient derived from *H. pluvialis* generally includes, but not limited to *H. pluvialis*. In general, the ingredient derived from *H. pluvialis* refers to all materials that made of *H. pluvialis*, such as its freeze-dried (lyophilized) powder, crude extract, astaxanthin clathrate, *H. pluvialis* oil, complex containing *H. pluvialis*, or any other commercially available ingredient containing *H. pluvialis*. Only if the weight percentage concentration of the astaxanthin of the ingredient derived from *H. pluvialis* is greater than 1%, the ingredient is suitable for use in the present invention. For the sake of explanation, the ingredient derived from *H. pluvialis* is hereinafter termed "*H. pluvialis* ingredient".

Specifically, in accordance with a preferred embodiment of the present invention, the weight percentage concentration of the *H. pluvialis* ingredient ranges preferably from 1% and 5%. According to a preferred embodiment of the present invention, when the astaxanthin clathrate is provided, the *H. pluvialis* ingredient can be at first dissolved in a solvent according to the predetermined weight percentage concentration of astaxanthin by stirring. When the *H. pluvialis* ingredient completely dissolves in the solvent after stirring, the solution of *H. pluvialis* is formed. It should be noted that the whole dissolving process and operation should protected from light and maintained in an inert gas atmosphere such as nitrogen or helium. The dissolved solution of *H. pluvialis* should be protected from light and stored at 4° C.-8° C. to prevent oxidation of astaxanthin. Next, the cyclodextrin is weighed according to the predetermined weight percentage concentration, and then dissolved in deionized water by stirring. When the cyclodextrin completely dissolves, a cyclodextrin solution is obtained for the subsequent steps. According to a preferred embodiment of the invention, the cyclodextrin is selected from the group consisting of alpha-cyclodextrin, beta-cyclodextrin or gamma-cyclodextrin and combinations thereof.

According to a preferred embodiment of the present invention, as for the preparation of polysaccharide, the polysaccharide is weighed according to the predetermined weight percentage concentration, and then dissolved in deionized water by stirring. When the polysaccharide completely dissolves, a polysaccharide colloid is obtained for the subsequent steps. Next, the solution of *H. pluvialis* and cyclodextrin solution are thoroughly stirred and mixed to form *H. pluvialis*-cyclodextrin mixture. Then, the *H. pluvialis*-cyclodextrin mixture is concentrated to remove most of the solvent and water content, and thus a concentrated paste is obtained. Next, the concentrated paste and the polysaccharide colloid are thoroughly stirred and mixed to form *H. pluvialis*-cyclodextrin-polysaccharide composite paste. Then, *H. pluvialis*-cyclodextrin-polysaccharide composite paste is dried to form the astaxanthin clathrate.

According to a preferred embodiment of the present invention, the aforementioned solvents include, but not limited to methanol, ethanol, acetone or any mixed solvent which contains those solvents, wherein the weight ratio of the *H. pluvialis* ingredient to the solvent is between 1:1000 and 1:10, preferably between 1:500 and 1:20. The dissolving temperature ranges from room temperature to 70° C., preferably from 30° C. to 60° C. The stirring time ranges from 1 minute to 120 minutes, preferably 5 minutes to 60 minutes.

According to a preferred embodiment of the invention, the weight ratio of cyclodextrin to water is between 1:200 and 1:5, preferably between 1:100 and 1:20. The dissolving temperature ranges from room temperature to 50° C. The stirring time ranges from 1 minute to 120 minutes, preferably 5 minutes to 60 minutes. In addition, in terms of the final product of astaxanthin compound composition, the weight percentage concentration of the cyclodextrin ranges from 0.5% to 3%. When the solution of H. pluvialis is mixed with the cyclodextrin solution, the stirring time ranges from 1 hour and 24 hours, preferably from 2 hours to 10 hours in order to mix these two solutions well. The mixing procedure should be protected from light and maintained in an inert gas atmosphere such as nitrogen or helium. The method of concentrating H. pluvialis-cyclodextrin mixture is not limited to specific approach, but preferably the mixture is concentrated under reduced pressure. The method of drying H. pluvialis-cyclodextrin-polysaccharide composite paste includes lyophilization, freeze drying, vacuum drying or atmospheric drying, to ultimately form the astaxanthin clathrate for being used according to the present invention.

According to a preferred embodiment of the present invention, the polysaccharide used in the present invention includes, but is not limited to hyaluronic acid, hyaluronan, sodium hyaluronate, gum arabic, modified starch, hydrolyzed starch, maltodextrin, alginate, carrageenan, chitin, chitosan, cellulose, or a combination of such polysaccharides. The weight ratio of the polysaccharide to water is between 1:1000 and 1:10, preferably between 1:200 and 1:50.

More specifically, according to a preferred embodiment of the present invention, the practical operation of preparing the astaxanthin clathrate includes the following steps. The H. pluvialis is extracted by means of solvent extraction or supercritical fluid extraction to obtain the H. pluvialis oil, which contains astaxanthin. The weight percentage concentration of astaxanthin to the H. pluvialis oil ranges from 1% to 20%. Take a 250 ml three-necked round-bottomed flask, cover the aluminum on the flask to protect it from light and fill in nitrogen gas, add 100 ml of solvent, and then add 0.2 g H. pluvialis oil sourced from H. pluvialis. In one embodiment, the weight percentage concentration of astaxanthin to H. pluvialis oil ranges from 1% to 20%. In another embodiment, the weight percentage concentration of astaxanthin to H. pluvialis oil ranges from 10% to 20%. In still another embodiment, the weight percentage concentration of astaxanthin to H. pluvialis oil ranges from 5% to 10%. In another preferred embodiment, the weight percentage concentration of astaxanthin to H. pluvialis oil ranges from 1% to 5%. The mixture is stirred at 50° C. for 30 minutes to dissolve H. pluvialis oil in the solvent to obtain the astaxanthin solution for later use. Next, a 500 ml beaker is taken, and 250 ml of pure water is added into the beaker. Then, the temperature of the pure water in the beaker is maintained at 50° C. Five grains (5 g) of β-cyclodextrin is added into the beaker to stir to dissolve the β-cyclodextrin in the pure water, After stirring 10 minutes, the β-cyclodextrin solution can be obtained for later use. Next, a 250 ml beaker is taken, and 100 ml of pure water is added into the beaker. Half gram (0.5 g) of polysaccharide (molecular weight: 2 million Dalton) is added into the beaker, and the temperature of the solution (pure water and the polysaccharide) in the beaker is maintained at 50° C. and the solution in the beaker is stirred for 30 minutes to prepare the polysaccharide colloid. Then, a 500 ml three-necked round-bottomed flask is taken, and the previously prepared β-cyclodextrin solution is poured into this flask. Then, the prepared β-cyclodextrin solution is heated and stirred at 50° C. The round-bottomed flask is protected from light by covering the aluminum foil and the nitrogen gas is filled into the round-bottomed flask. Next, the previously prepared astaxanthin solution is dropped slowly into the round-bottomed flask within a time period of 10 minutes. After completing the dropwise addition, the mixture is stirred continuously for 3 hours to form the astaxanthin-β-cyclodextrin complex. Thereafter, the astaxanthin solution is poured into a 500 ml round-bottomed concentration flask and then the solution is concentrated under reduced pressure to obtain the concentrated paste.

A 250 ml beaker is taken the above concentrated paste, and the polysaccharide colloid are added into the beaker to stir for 30 minutes to form the astaxanthin-β-cyclodextrin-polysaccharide complex colloid. Finally, the astaxanthin-β-cyclodextrin-polysaccharide complex colloid is poured into a plastic flat plate to dry under vacuum at room temperature for 24 hours to obtain an astaxanthin-β-cyclodextrin-polysaccharide complex. After drying, the dried product can be further grounded and sieved to obtain the powdered astaxanthin clathrate.

It has been known that multiple active ingredients can be used in combination with medicinal materials of traditional Chinese medicine to improve the health benefits. According to the present invention, the extract of Chinese wolfberry extract and the jujube extract are further utilized as active components. Besides, an amino acid such as arginine can also be used to elaborate the effects on regulating lipid profiles of the astaxanthin compound composition according to the present invention. It is generally known that the Chinese wolfberry contains carotene, betaine, vitamin A, vitamin B1, vitamin B2, vitamin C, calcium, phosphorus, and iron etc. Pharmacological studies reveal that the wolfberry is beneficial to cardiovascular health. Jujube is rich in vitamin C, protein, fat, saccharide, vitamin B, calcium, iron, triterpenes and cyclic AMP. Pharmacological studies have confirmed that jujube has effects of liver protection, improving blood oxygen, and reinforcing the blood vessels, etc.

According to the concept of the compound composition, the mixing unit 14 of the astaxanthin compound composition preparation 10 of the present invention further adds Chinese wolfberry extract, the jujube extract and the amino acid to the aforementioned astaxanthin clathrate and mixes them well to form a compound mixture. Regarding the source and selection of Chinese wolfberry extract and the jujube extract, it is not particularly limited. Those kinds of extract may be obtained by extracting from raw materials of Chinese wolfberry and jujube plant; and may also be products/raw materials of commercially available Chinese wolfberry extract and jujube extract.

According to the present invention, the kind of the amino acid used in the mixing unit 14 is not particularly limited, as long as it is beneficial to the human body, including but not limited to essential amino acids. The essential amino acids include, but are not limited to tryptophan, valine, threonine, lysine, phenylalanine, leucine, isoleucine, methionine, histamine, arginine, etc. For the modern busy lifestyle which is labor-consuming, people need a lot of nutrition, therefore, arginine is a preferable selection.

Finally, in order to improve the overall stability, activity and shelf life of the health products, the additive-adding unit 16 of the astaxanthin compound composition preparation system 10 of the present invention further adds an anticaking agent to the compound mixture to form the astaxanthin compound composition. The weight percentage concentration of anticaking agent in astaxanthin compound composition ranges from 0.5% to 3%. Regarding the selection of the anticaking agent, there is no limitation, as long as it is a legally added anticaking agent which is suitable for use in the present invention. More specifically, according to a preferred embodiment of the present invention, any solid substance (can be any forms such as granules or powders) that have porous structure and can absorb oily substances is suitable for being used in the present invention, for example, calcium silicate, silicon dioxide, potassium ferrocyanide, tricalcium phosphate, magnesium oxide, microcrystalline cellulose, cyclodextrin, activated charcoal, and kaolin, etc. For those skilled persons in this technical field, they can also use any combinations of abovementioned options of anticaking agent according to any purpose and effect of the anticaking agent. According to a preferred embodiment of the present invention, either the anticaking agent calcium silicate or silicon dioxide may be added singly, or both the anticaking agent, i.e., calcium silicate and silicon dioxide, may be added. The more effective way is to add both calcium silicate and silicon dioxide together as they can not only prevent astaxanthin compound composition from caking, but also can absorb oily substance and moisture more effectively, and thereby the fluidity can be improved, therefore it facilitates the subsequent processing of the astaxanthin compound composition.

After obtaining the astaxanthin compound composition, suitable filling, tableting or processing process can be applied according to the product forms. The astaxanthin compound composition can be further processed to manufacture various dosage forms for final products, such as hard capsules, soft capsules, powder packets, tablets, and drinks, etc. The details of the related filling, tableting or processing processes are well known to the skilled persons in the art, and will not be described in detail herein.

The astaxanthin compound composition prepared by the astaxanthin compound composition preparation 10 of the present invention is excellent in regulating lipid profile, which is partially supported by the following experimental examples.

Experimental Example 1: Animal Experiments on Lowering Blood Lipids

Male Syrian hamsters aged 6-7 weeks were tested for evaluating the effects of lowering blood lipid profile. Animals were divided into 6 groups, 8 hamsters in each group with a total of 48 hamsters. The experiment was conducted for 8 weeks, and the dosing method was oral gavage, and the animals of experimental groups were fed with the astaxanthin compound composition prepared according to the present invention. The dosage used was calculated according to the dosage for adult human. Practically, as for an adult human whose body weight is 60 kg, he/she would be suggested to take 250 mg of the astaxanthin compound composition per day. Based on this dosage, the 1×, 2× and 3× dosages were respectively defined for the following testing. The animals were fed with 1× (the converted dosage for hamster is 30.83 mg/kg), 2× (the converted dosage for hamster is 61.67 mg/kg) and 3× (the converted dosage for hamster is 92.50 mg/kg) dosages. At the same time, the clinically used anti-hyperlipidemic drug, Probucol, was used as comparison for evaluating the anti-hyperlipidemic effect. The overall experimental design and grouping are shown in Table 1.

TABLE 1

Experimental design and animal grouping for evaluating the anti-hyperlipidemic effect

| Groups (Code) | Diet Type | Dosing Substance | Dosage for animals body (mg/kg weight) |
|---|---|---|---|
| Normal control (NOR) | normal diet | RO Water | — |
| Vehicle control (HC) | high cholesterol diet | RO Water | — |
| Positive control (P) | high cholesterol diet | Probucol | 124 |
| AL (1X dosage) | high cholesterol diet | astaxanthin compound composition Powder | 30.83 |
| AM (2X dosage) | high cholesterol diet | astaxanthin compound composition Powder | 61.67 |
| AH (3X dosage) | high cholesterol diet | astaxanthin compound composition Powder | 92.50 |

Biostatistical analysis method: the results of the experiment were statistically tested based on one-way ANOVA by using SPSS 10.1 system. Then, the difference among the groups was tested by Duncan's Multiple Range Test. When the p value is smaller than 0.05 ($P<0.05$), it indicates statistically significant difference.

Result 1: Changes of Total Cholesterol and Triglyceride Concentrations in Blood.

The experimental animals were sacrificed to have blood drawn and the results of total cholesterol (TC) and triglyceride (TG) were shown in Table 2. The total cholesterol and triglyceride in normal control group were significantly lower than those in vehicle control Group ($p<0.05$). It indicated that the high cholesterol diet of vehicle control group successfully caused hyperlipidemia signs in those animals. Regarding the results of the experimental group, the results of the total cholesterol showed that the results of AM (2× dosage) group, the AH (3× Dosage) group and the positive control group were significantly lower than vehicle control group ($p<0.05$). The results of triglyceride showed that the results of AM (2× dosage) group significantly lower than the vehicle control group ($p<0.05$). On the basis of abovementioned results, the astaxanthin compound composition prepared according to the present invention, at 2× dosage, significantly lowered the elevated total cholesterol in serum resulted from high cholesterol diet ($p<0.05$). Furthermore, when the dosage of astaxanthin compound composition came up to 3× dosage, it further significantly lowered the triglyceride.

TABLE 2

Effects on total cholesterol (TC), triglyceride (TG), high-density lipoprotein cholesterol (HDL-C), low-density lipoprotein cholesterol (LDL-C) and the ratio of LDL-C/HDL-C in serum of hamster dosed with different substances.

| Group (Code) | TC (mg/dL) | TG (mg/dL) | HDL-C (mg/dL) | LDL-C (mg/dL) | LDL-C/HDL-C | LDL-C/TC | HDL-C/TC |
|---|---|---|---|---|---|---|---|
| Normal control | 85 ± 9 | 79 ± 10 | 49 ± 4 | 10.8 ± 3.3 | 0.217 ± 0.055 | 0.124 ± 0.027 | 0.771 ± 0.045 |

TABLE 2-continued

Effects on total cholesterol (TC), triglyceride (TG), high-density lipoprotein cholesterol (HDL-C), low-density lipoprotein cholesterol (LDL-C) and the ratio of LDL-C/HDL-C in serum of hamster dosed with different substances.

| Group (Code) | TC (mg/dL) | TG (mg/dL) | HDL-C (mg/dL) | LDL-C (mg/dL) | LDL-C/HDL-C | LDL-C/TC | HDL-C/TC |
|---|---|---|---|---|---|---|---|
| (NOR) Vehicle control | 177 ± 9 | 155 ± 30 | 89 ± 4 | 43.9 ± 3.2 | 0 494 ± 0.044 | 0.247 ± 0.011 | 0.670 ± 0.038 |
| (HC) Positive control (P) | 157 ± 11 | 152 ± 14 | 83 ± 11 | 31.8 ± 3.9 | 0.392 ± 0.110 | 0.203 ± 0.032 | 0.707 ± 0.066 |
| AL (1X dosage) | 162 ± 17 | 134 ± 24 | 85 ± 7 | 37.9 ± 3.8 | 0.444 ± 0.041 | 0.234 ± 0.018 | 0.705 ± 0.037 |
| AM (2X dosage) | 141 ± 15 | 136 ± 21 | 78 ± 10 | 36.8 ± 3.6 | 0.482 ± 0.091 | 0.263 ± 0.040 | 0.799 ± 0.055 |
| AH (3X dosage) | 141 ± 24 | 112 ± 21 | 79 ± 12 | 38.5 ± 5.5 | 0.490 ± 0.047 | 0.275 ± 0.023 | 0.803 ± 0.039 |

Result 2: Changes of HDL-C and LDL-C in Blood

Please continue to refer to Table 2 for the effects of astaxanthin compound composition on high-density lipoprotein cholesterol (HDL-C), low-density lipoprotein cholesterol (LDL-C) in hamsters fed with high cholesterol diet. The vehicle control group was fed with high cholesterol diet, and thus the HDL-C and LDL-C were significantly increased compared to the normal control group (p<0.05). As for the AL (1× dosage) group, AM (2× dosage) and AH (3× dosage), the LDL-C concentrations were all significantly lower than the vehicle control (P<0.05).

TABLE 3

Effects on total cholesterol (TC), triglyceride (TG) in the liver and feces of hamster dosed with different substances.

| | liver | | feces | |
|---|---|---|---|---|
| Group (Code) | TC (mg/g) | TG (mg/g) | TC (mg/g) | TG (mg/g) |
| Normal control (NOR) | 3.40 ± 0.31 | 16.3 ± 1.9 | 7.8 ± 1.6 | 17.0 ± 2.4 |
| Vehicle control (HC) | 4.92 ± 0.77 | 16.7 ± 2.7 | 13.8 ± 4.2 | 17.5 ± 8.3 |
| Positive control (P) | 3.80 ± 0.26 | 13.7 ± 1.5 | 6.7 ± 0.9 | 15.8 ± 2.8 |
| AL (1X dosage) | 3.76 ± 0.41 | 15.5 ± 3.1 | 7.3 ± 1.3 | 15.9 ± 2.9 |
| AM (2X dosage) | 3.62 ± 0.26 | 16.2 ± 2.2 | 9.4 ± 1.2 | 14.7 ± 2.5 |
| AH (3X dosage) | 3.56 ± 0.37 | 14.6 ± 1.9 | 8.1 ± 0.9 | 14.5 ± 2.8 |

Result 3: Changes of Total Cholesterol (TC), Triglyceride (TG) in the Liver and Feces.

When the concentration of total cholesterol and triglyceride in the liver is too high, the risk of developing fatty liver may increase. According to the present Experimental Example, the concentration changes in total cholesterol and triglyceride in the liver and feces of the tested animals are shown in Table 3. Due to that the vehicle control group was fed with high cholesterol diet, the total cholesterol was significantly higher than that of normal control group (p<0.05). Among the AL (1× dosage) group, AM (2× dosage) group, AH (3× dosage) group, and positive control (P) group, the total cholesterol concentration in the liver of the tested animals was significantly lower than vehicle control group (p<0.05). This observation indicates that the astaxanthin compound composition may have the effect on preventing fatty liver.

The decreased concentrations of cholesterol and triglyceride might be due to that the production or absorption mechanism were inhibited; or might be due to that those substances were excreted through feces. Therefore, by measuring the concentrations of total cholesterol and triglyceride in the feces of tested animals, the effects of the astaxanthin compound composition on promoting the excretion of cholesterol and triglyceride can be revealed. According to the experimental results, the concentrations of total cholesterol of the animal's feces in the AL (1× dosage) group, AM (2× dosage) group, AH (3× dosage) group are measured, and the results showed that the concentrations of total cholesterol in all the three groups were significantly lower than the vehicle control group (P<0.05); however, the concentration of triglyceride in the feces was not significantly affected (P>0.05). These results indicated that taking the dry powder of astaxanthin compound composition might reduce the synthesis of cholesterol, and thereby reduce the concentration of triglyceride in the feces.

Although specific embodiments have been illustrated and described, it will be obvious to those skilled in the art that various modifications may be made without departing from what is intended to be limited solely by the appended claims.

What is claimed is:

1. A capsule consisting essentially of a *Haematoccus pluvialis* extract, a red date extract, and a wolfberry extract; wherein the *Haematoccus pluvialis* extract is 10% to 90% of the capsule, the red date extract is 0.1% to 5% of the capsule and the wolfberry extract is 0.1% to 5% of the capsule.

2. The capsule of claim 1, further consisting essentially of a polysaccharide selected from the group consisting of hyaluronic acid, hyaluronan, sodium hyaluronate, gum arabic, maltodextrin, alginate, carrageenan, chitin, chitosan, cellulose, and combinations thereof.

3. The capsule of claim 1, further consisting essentially of a component selected from the group consisting of calcium silicate, silicon dioxide, potassium ferrocyanide, tricalcium phosphate, magnesium oxide, microcrystalline cellulose, cyclodextrin, activated charcoal, kaolin and combinations thereof.

4. A method of making the capsule of claim 1, consisting essentially of mixing a red date extract, a wolfberry extract, a Haematoccus pluvialis extract and combining them at the claimed amounts in a capsule to produce the capsule of claim 1.

* * * * *